United States Patent [19]
Reischl et al.

[11] 4,336,365
[45] Jun. 22, 1982

[54] PROCESS FOR THE CONTINUOUS PREPARATION OF POLYISOCYANATES CONTAINING URETDIONE GROUPS AND THEIR USE AS STARTING COMPONENTS FOR THE PRODUCTION OF POLYURETHANE RESINS

[75] Inventors: Artur Reischl; Bernd Quiring; Claus Rathjen, all of Leverkusen, Fed. Rep. of Germany

[73] Assignee: Bayer Aktiengesellschaft, Leverkusen, Fed. Rep. of Germany

[21] Appl. No.: 230,782

[22] Filed: Feb. 2, 1981

[30] Foreign Application Priority Data

Feb. 12, 1980 [DE] Fed. Rep. of Germany ....... 3005106

[51] Int. Cl.³ ............................................. C08G 18/00
[52] U.S. Cl. ...................................... 528/44; 252/182; 526/230; 528/67; 528/272; 528/421
[58] Field of Search ........................ 526/230; 252/182; 528/272, 421, 44, 67; 260/239 AR

[56] References Cited

U.S. PATENT DOCUMENTS 3,793,238 2/1974 Winkelmann et al. ........ 260/2.5 AY
3,923,743 12/1975 Quiring et al. .................. 260/75 NT
3,993,641 11/1976 Tiemann et al. ................ 260/239 A
4,044,171 8/1977 Müller et al. ......................... 427/27
4,076,627 2/1978 Friedrichs ........................... 210/499

OTHER PUBLICATIONS

Kunststoff-Handbuch, vol. VII, Polyurethane, published by Vieweg-Höchtlen Carl-Hanser-Verlag, Munich, 1966-p. 16.

*Primary Examiner*—Maurice J. Welsh
*Attorney, Agent, or Firm*—Gene Harsh; Joseph C. Gil; Richard A. Elder

[57] ABSTRACT

The instant invention is directed to a process for the continuous preparation of polyisocyanates containing uretdione groups comprising dimerizing aromatic polyisocyanates which are free from uretdione groups in the presence of catalysts which accelerate the dimerization of isocyanates, at −30° to 90° C. in a self-cleaning, coolable screw reactor with continuous feeding in of the free polyisocyanate and of the dimerization catalyst, and in the presence of from 3 to 90% by weight, based on the whole mixture, of an additive containing hydroxyl groups, which additive comprises either (i) a compound within the molecular weight range of from 62 to 10,000 containing at least one hydroxyl group or (ii) a mixture of several compounds having an average molecular weight within the range of from 62 to 10,000 containing at least one bound hydroxyl group, wherein said hydroxyl-containing compound or compounds are added to the reaction mixture before the isocyanate used as starting material solidifies due to the dimerization reaction.

4 Claims, No Drawings

PROCESS FOR THE CONTINUOUS PREPARATION OF POLYISOCYANATES CONTAINING URETDIONE GROUPS AND THEIR USE AS STARTING COMPONENTS FOR THE PRODUCTION OF POLYURETHANE RESINS

BACKGROUND OF THE INVENTION

This invention relates to a process for the continuous preparation of isocyanates containing uretdione groups by the dimerization of polyisocyanates in the presence of compounds containing one or more hydroxyl groups with the addition of dimerization catalysts. The invention also relates to the use of the products of the process for the production of polyurethane plastics.

The preparation of polyfunctional uretdione isocyanates in the presence of dimerization catalysts is known (see Kunststoff-Handbuch, Volume VII, Polyurethane, published by Vieweg-Höchtlen, Carl-Hanser-Verlag, Munich, 1966, page 16).

In German Offenlegungsschrift No. 2,452,390 and U.S. Pat. No. 3,993,641, the dimerization reaction is carried out in a continuously operating reaction screw which can be cooled. In this method, the polyisocyanate which contains uretdione groups, e.g. dimerized 2,4-tolylene diisocyanate, is obtained in the form of a powder. For many types of processing, this powder is not sufficiently fine until it is ground down. This method of preparation also causes heavy wear in the screw due to abrasion, which can be recognized, for example, by loud squeaking noises in the operating part of the screw.

In the method described above, it is difficult to remove the considerable heat of reaction by means of the pulverulent product which has little thermal conductivity. If a pure dimer is to be obtained, certain, relatively low temperatures must not be exceeded. It will be obvious that in large machines this condition results in uneconomical throughputs. The addition of inert plasticizing agents proposed in U.S. Pat. No. 3,993,641 results in plastics which contain external plasticizers, with all the concomitant disadvantages such as exudation, a high content of extractable substances and end products which gradually become brittle.

A process has now surprisingly been found by which uretdione polyisocyanates whose end products do not have the disadvantages mentioned above can be obtained in a very finely divided form at high machine throughputs in a single operating step, using isocyanate reactive compounds as dispersing agents.

DESCRIPTION OF THE INVENTION

The present invention relates to a process for the continuous preparation of polyisocyanates containing uretdione groups comprising dimerizing aromatic polyisocyanates which are free from uretdione groups in the presence of catalysts which accelerate the dimerization of isocyanates, at −30° to 90° C. in a self-cleaning, coolable screw reactor with continuous feeding in of the free polyisocyanate and of the dimerization catalyst, and in the presence of from 3 to 90% by weight, based on the whole mixture, of an additive containing hydroxyl groups, which additive comprises either (i) a compound within the molecular weight range of from 62 to 10,000 containing at least one hydroxyl group or (ii) a mixture of several compounds having an average molecular weight within the range of from 62 to 10,000 containing at least one bound hydroxyl group, wherein said hydroxyl-containing compound or compounds are added to the reaction mixture before the isocyanate used as starting material solidifies due to the dimerization reaction.

The present invention also relates to the use of products obtained by this process as starting components in the production of polyurethane plastics by the isocyanate poly-addition process.

Screw extruders of the type known in the art, which have been described e.g. by H. Herrmann in "Schneckenmaschinen in der Verfahrenstechnik" published by Springer Verlag, Berlin-Heidelberg-New York, 1972, pages 161–170 are suitable for carrying out the process according to the invention. Multishaft screw extruders, particularly two-shaft extruders with double or triple threads and with intermeshing screw shafts rotating in the same sense and constantly scraping against each other and against the internal wall of the screw housing are particularly suitable, for example those described in German Pat. No. 862,668.

The screw shafts are advantageously equipped not only with helical "conveyor elements" but also with special "kneading elements" placed for example at a short distance downstream of the inlet, viewed in the direction of delivery. These elements increase the shearing and mixing action and have been described for example in German Pat. Nos. 813,154 and 940,109. Kneading elements of this type may also advantageously be provided at other parts of the extruder, for example near the product outlet.

In the process according to the invention, the starting materials may first be mixed by means of suitable commercial pumps such as piston, membrane, rotary slide or gear wheel pump. The solid substances are fed continuously in the required proportions into the coolable, and optionally also heatable, screw reactor by means of suitable devices for feeding solids, such as vibrating chutes, dosing screws or balancing conveyors.

Although the temperature in the reactor should not rise above a certain, relatively low value in order to avoid the formation of by-products such as isocyanurate resins, it is occasionally advantageous to feed the raw materials at an elevated temperature into the screw reactor. This is particularly advantageous if, for example, the starting product is not liquid at room temperature.

The starting compounds used for the process according to the invention include in particular aromatic polyisocyanates corresponding to the formula $$R(NCO)_n$$

in which
n represents an integer or (if isocyanate mixtures at a statistical mean are used) any number in the range of 1.5 to 3, preferably 2, and
R represents an aromatic hydrocarbon group having a total of 6 to 30 carbon atoms which may be substituted by one or more alkyl, cycloalkyl, alkoxy, phenoxy or halogen groups and/or may carry alkylene groups as bridge members between aromatic rings, and it preferably represents an aromatic hydrocarbon group having a total of from 6 to 15 carbon atoms which may be methyl substituted or carry methylene bridges.

Examples of such aromatic diisocyanates include 2,4-diisocyanatotoluene, 2,6-diisocyanatotoluene, mixtures of these isomers, 4,4'-diisocyanatodiphenylmethane which may be substituted with alkyl or halogen, and isomers of these diisocyanates, 4,4'-diisocyanatodiphenylpropane, 1,4-diisocyanato-2-chloro-benzene, 4,4'-diisocyanato-3,3'-dichlorodiphenylmethane, 1,4-diisocyanato-3-methoxy-benzene, 1,4-diisocyanato-3-phenoxybenzene and diisocyanatodimethyl-diphenyl. The following diisocyanates are preferred for the process according to the invention: 2,4-diisocyanatotoluene, 2,6-diisocyanatotoluene, mixtures of these isomers, and 4,4'-diisocyanatodiphenylmethane. 2,4-Diisocyanatotoluene is particularly preferred. Monofunctional isocyanates such as phenyl or p-tolyl-isocyanate may also be used in special cases in quantities of up to 50 isocyanate equivalents percent, based on the total quantity of isocyanates used as starting material. Trifunctional and higher functional aromatic polyisocyanates such as the higher than difunctional polyisocyanates of the diphenylmethane series which are invariably present in the phosgenation products of aniline-formaldehyde condensates may also be used, preferably as components of a mixture. Such phosgenation products are then used as polyisocyanate components for the process according to the invention. Modified polyisocyanates containing urethane or urea groups may also be used, e.g. the addition product of 5 mol of 4,4'-diphenylmethane diisocyanate and 1 mol of tripropylene glycol. When high melting diisocyanates are used, small quantities of organic solvents may be useful to lower the melting point. It is preferred to use polyisocyanates which are liquid under the temperature conditions of the process according to the invention.

Mixtures of the above-mentioned diisocyanates may, of course, also be used.

The additives which are an essential feature of the invention are either (i) organic compounds within the molecular weight range of 62 to 10,000 having at least one alcoholic hydroxyl group or (ii) mixtures of compounds having an average molecular weight of 62 to 10,000 which have at least one alcoholic hydroxyl group.

Preferred additives of type (i) are compounds with molecular weights of from 400 to 6000 having two or three alcoholic hydroxyl groups, in particular difunctional or trifunctional aliphatic polyether polyols or polyester polyols within this molecular weight range.

Preferred additives of type (ii) are mixtures of organic compounds with an average molecular weight in the range of 400 to 6000 having an average hydroxyl functionality of from 1.5 to 3 and containing at least one alcoholic hydroxyl group. Most preferred are alkane polyols with molecular weights of 62 to 400 and polyol mixtures having an average hydroxyl functionality of from 2 to 3 and an average molecular weight of from 400 to 6000 containing polyether and/or polyester polyols of the last-mentioned type.

Any of the compounds which have hydroxyl groups may in principle be used as these additives according to the invention, in particular the preferred polyether and polyester polyols already mentioned above, optionally as mixtures with simple alkane polyols. Also suitable but less preferred are polythioether polyols, polyacetal polyols and polycarbonate polyols, hydroxyl group-containing polymers such as polyhydroxypolyacrylates, and natural oils containing hydroxyl groups.

Suitable hydroxyl compounds used alone or as mixtures include, for example, divalent and trivalent low molecular weight alcohols (such as ethylene glycol, propylene glycol, butylene glycol, hexamethylene glycol, and dialkylene), trialkylene or higher polyalkylene glycols, glycerol or trimethylolpropane as well as the known high molecular weight polyhydroxyl compounds of polyurethane chemistry. Polyester polyols and polyether polyols such as those which are exemplified in U.S. Pat. No. 4,033,912, column 5, line 14 to column 6, line 12 and in the literature cited there are particularly preferred. Examples of the above-mentioned polyhydroxyl compounds which are suitable but less preferred are to be found in U.S. Pat. No. 4,033,912, column 6, lines 13 to 56 and in the literature cited there. In addition to these polyhydroxyl compounds, monohydric alcohols such as n-butanol, isooctanol or n-dodecanol may also be used as additives (i) although it is less advantageous to use such hydroxyl compounds as the only additives than to use higher functional polyols. If an alcohol mixture (ii) is used as the essential additive according to the invention, the mixture may contain monohydric alcohols such as methanol, ethanol or the last mentioned monohydric alcohols, provided the above-mentioned conditions as regards the average hydroxyl functionality and the average molecular weight are observed.

The essential additives according to the invention may contain other isocyanate reactive groups in addition to the hydroxyl groups, in particular groups such as urethane, carboxyl or mercapto groups, provided that these additional isocyanate reactive groups do not have a higher reactivity with isocyanate groups than the hydroxyl groups. It is however preferred, to use additives (i) or (ii) in which the isocyanate reactive groups consist exclusively or virtually exclusively of hydroxyl groups.

The hydroxyl compounds used in the process according to the invention are, in particular, compounds of this type which are liquid under the temperature conditions of the process, in particular at temperatures below 80° C. and most preferably below 55° C.

The compounds containing hydroxyl groups which are used as essential additives according to the invention are put into the process in quantities of from 3 to 90% by weight, preferably from 5 to 70% by weight, most preferably from 10 to 60% by weight, based on the whole mixture.

The catalysts used for the process according to the invention may be any substances capable of accelerating the dimerization of aromatic polyisocyanates resulting in the formation of uretdione groups. Tertiary aliphatic and heterocyclic amines such as triethylamine, tri-n-propylamine, N-methylmorpholine and N-ethylmorpholine and pyridine are preferred. It is particularly preferred to use phosphines corresponding to the formula

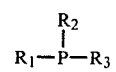

in which $R_1$ represents an aliphatic hydrocarbon group having from 1 to 18 carbon atoms and $R_2$ and $R_3$, which may be the same or different, represent an aliphatic hydrocarbon group having from 1 to 18 carbon atoms or a phenyl group.

The catalysts are used in such quantities in the process according to the invention that the dimerization reaction is completed virtually quantitatively within 60 minutes, preferably within 1 to 3 minutes, at the reaction temperature which will be defined in more detail below. The catalysts are generally used in quantities of from 0.001 to 3% by weight, preferably from 0.05 to 2.5% by weight, based on the dimerizing starting diisocyanate. For accurately measuring out small quantities of catalyst, it is advantageous to dissolve the catalyst in an organic solvent but the quantity of solvent used should not exceed 20% by weight and preferably should not exceed 5% by weight, based on the isocyanate.

The process according to the invention is preferably carried out solvent-free although the small quantity of solvent mentioned above which may be used for dissolving the catalyst does not interfere with the process. These small quantities of solvent may easily be removed by evaporation during or after the reaction in the screw extruder. Larger quantities of catalyst may, of course, be used if the rates of throughput are extremely high and particularly under conditions of intensive cooling. The aim is to use as little catalyst as possible in order to obtain a product with a high degree of purity.

It is essential to maintain a temperature in the range of from $-30°$ to $90°$ C. This can easily be achieved by equipping the reactor with several temperature zones which can be adjusted independently of each other. It is necessary to cool most vigorously where the largest quantity of heat is released. At the same time, the temperature must not be kept too low because the reaction velocity is then too slow. The reactor may even be heated at the inlet if necessary, i.e. when solid starting product is to be melted before the reaction.

The temperature of the reaction product must not exceed $90°$ C. during uretdione formation and before destruction of the catalyst. Reaction temperatures ranging from $-20°$ to $70°$ C. and particularly from $0°$ to $60°$ C. are preferred.

After completion of the reaction, the catalyst is generally destroyed with catalyst poisons such as alkylating agents, elementary sulfur, atmospheric oxygen or compounds which release oxygen. This may be carried out for example in a mixer, kneader or extruder. According to a preferred method, the catalyst is destroyed at the end of the reaction screw in which uretdione formation is carried out. For many of the applications of the products produced by the process according to the invention, however, the catalyst may be left in the end product.

The starting polyisocyanate and the hydroxyl compounds used as essential additives according to the invention are either fed separately into the screw extruder or first mixed (for example in a throughflow mixer). The catalyst is preferably measured into the already homogeneous mixture of polyisocyanate and hydroxyl compound or it may also be dissolved or uniformly distributed in the additive. It would in principle be possible to add the additive or a part thereof to the reaction mixture downstream of the extruder inlet, at any point before solidification of the starting isocyanate takes place.

According to the invention, the product temperatures in the screw reactor are within the range of $-30°$ to $90°$ C. and the speeds of rotation of the screw shafts are generally from 20 to 300/min.

According to a preferred embodiment of the process of the invention, the reaction is controlled, for example by adjustment of the speed of rotation of the screw, the rate of throughput and/or the reaction temperature, so that the catalyst is destroyed even before the reaction is completed, preferably while it is still inside the reaction screw. The reaction may be controlled in such a manner that a conversion rate of, for example, 30 or 70%, and preferably at least 50% is obtained. This method has the advantage that the number of side reactions is kept particularly small and a relatively low viscosity paste which is easy to handle is obtained.

In another special embodiment of the process, another, preferably liquid polyisocyanate, in particular of the type exemplified above, is added, preferably continuously, during or after destruction of the catalyst and is optionally reacted with the hydroxyl groups of the additive, preferably at temperatures below $80°$ C.

It is surprising that the uretdione polyisocyanate prepared by the process is obtained in the form of very finely divided pastes or powders in the screw reactor and the additive containing hydroxyl groups functions virtually only as dispersing agent. The reaction between isocyanate groups and hydroxyl groups which could have resulted in uretdione polyisocyanates heavily contaminated with bisurethanes and oligourethanes, would have had some influence on the softening range of the dimerization product. This polyaddition reaction which one would obviously have expected to take place does not occur, however, or is negligible compared with the formation of dimer. The uretdione polyisocyanates obtained by the process are not in the form of coarse lumps such as those obtained by solvent-free dimerization, but are so finely dispersed that they need not be milled down any further for subsequent processing.

In order to obtain an economical rate of throughput, the reaction may be completed in a second reactor of the same or different type, which is arranged downstream of the multishaft screw extruder. It is preferably operated continuously. The dimerization catalyst may be destroyed in this second reactor and/or the reaction product may be mixed therein with another, preferably liquid, substance which will not react with the uretdione polyisocyanate under the conditions employed.

According to a special embodiment of the process, the products of the process may be mixed with other hydroxyl compounds of the type exemplified above, during or after destruction of the catalyst. For example, in order to adjust the equivalent ratio of isocyanate groups and uretdione groups on the one hand to hydroxyl groups on the other, depending on the purpose for which the end products are finally intended so that, for example, systems which can be converted into high molecular weight polyurethane plastics by heat are obtained directly as end products. Such systems can also be obtained without the subsequent addition of a second polyisocyanate component if the equivalent ratio of isocyanate groups in the starting polyisocyanate to the hydroxyl groups in the additive is in the region of 1:1. In general, however, when carrying out the process according to the invention, the quantitative proportions of the individual components will be calculated to provide an excess of isocyanate groups and uretdione groups over hydroxyl groups. This excess may subsequently be further increased, as already explained, by the further addition of polyisocyanate after the dimerization reaction. Such systems which contain an excess of isocyanate groups and uretdione groups over hydroxyl groups, are suitable as polyisocyanate components for the production of polyurethane plastics by the isocyanate polyaddition process. These systems contain both free isocyanate groups, i.e. centers which are reactive with a polyhydroxyl component at room temperature or only moderately elevated temperature, and uretdione groups which, as is well known, react with hydroxyl groups only at elevated temperatures. These products according to the invention are thus particularly suitable for the production of polyurethane plastics by a two-step process in which a preliminary product which is still deformable is first obtained by reaction with a polyhydroxyl compound at room temperature or moderately elevated temperature and this preliminary product is then converted into its final, cross-linked state by the action of heat. When only small quantities of the essential additive according to the invention are used, the process results in pulverulent end products which are very suitable for the preparation of powder lacquers, particularly in combination with solid polyhydroxyl compounds wich can be pulverized. For the preparation of such powder lacquers it is advisable to use small quantities of the essential additives (i) or (ii) within the limits indicated above and subsequently to add polyhydroxyl compounds which are solid at room temperature, for example, polyester polyols which are solid at room temperature.

The products may also be modified by the addition of other auxiliary agents such as solvents, plasticizers, dyes, emulsifiers, inorganic or organic fillers, levelling agents, stabilizers or antioxidants. These additives may be introduced, for example, at the beginning or end of the screw extruder.

The products of the process may also be used to improve the bond strength of synthetic materials, including the bond between rubber and cord.

EXAMPLES

EXAMPLE 1

Tolylene-2,4-diisocyanate which has been heated to about 40° C., and a difunctional polyether polyol which has been obtained by the addition of propylene oxide and ethylene oxide to propane-1,2-diol and carries predominantly primary hydroxyl groups as end groups and has an average molecular weight of about 4000, are continuously fed in proportions by weight of 8:2 into the hopper of a double shaft laboratory screw reactor having an external shaft diameter of 32 mm and a length of about 1216 mm. 1.3% of tributylphosphine, based on the quantity of tolylene diisocyanate, are continuously fed into the second of five housings. The experimental data are entered in Table 1. 0.003 Parts by weight of sulfur for each part by weight of product are kneaded into the highly viscous paste in a short compounding screw. The solid particles have a particle size below 0.02 mm.

TABLE 1

| Example | 1A | 1B | 1C |
|---|---|---|---|
| Total throughput (kg/h) | 12 | 15 | 24 |
| Shaft speed (min$^{-1}$) | 150 | 175 | 275 |
| Dwell time approx. (min) | 2.1 | 1.6 | 1.1 |
| Housing temperatures (°C.) | | | |
| Housing 2 | 23 | 25 | 24 |
| Housing 3 | 12 | 12 | 9 |
| Housing 4 | 16 | 17 | 16 |
| Housing 5 | −14 | −14 | −14 |
| Product outlet temperature (°C.) | 30 | 35 | 44 |
| Yield (%)[1] | 88 | 89 | 99 |

[1] Yield of uretdione diisocyanate based on the quantity of tolylene diisocyanate put into the process.

EXAMPLE 2

Tolylene-2,4-diisocyanate heated to about 40° C. and the copolyether described in Example 1 are continuously fed in proportions by weight of 95:5 into the feed hopper of the screw reactor described in Example 1. 1.3% by weight of tributylphosphine (calculated on the diisocyanate) are fed into the second housing. The particle size of the uretdione diisocyanate produced is below 0.03 mm. The experimental conditions are summarized in Table 2.

TABLE 2

| Example | 2A | 2B | 2C |
|---|---|---|---|
| Total throughput (kg/h) | 12 | 18 | 24 |
| Shaft speed (min$^{-1}$) | 130 | 190 | 225 |
| Dwell time approx. (min) | 2.1 | 1.4 | 1.0 |
| Housing temperature (°C.) | −16 to +12 | −16 to +20 | −15 to +12 |
| Product outlet temperature (°C.) | 20 | 49 | 55 |
| Yield (%) | 97 | 96 | 96 |

EXAMPLE 3

The procedure is the same as described in Example 2 but using tolylene diisocyanate and polyether in proportions by weight of 1:1. A very sticky paste is obtained, in which the particles of uretdione diisocyanate have a diameter below 0.02 mm.

EXAMPLE 4

The mixture of 8 parts by weight of 2,4-tolylene diisocyanate and 3.6 parts by weight of the polyether described in Example 1 obtained in a short static mixer and heated to 40° C. is fed into the feed hopper of the screw reactor according to Example 1, 1.3% by weight (based on the quantity of tolylene diisocyanate) of tributyl phosphine are fed into the second housing of the reactor and a thoroughly stirred suspension of 0.048 parts by weight of sulfur in 0.4 parts of the same polyether is fed into the middle of the screw reactor. 5 Parts by weight of a crude 4,4'-diisocyanatodiphenylmethane which is liquid at room temperature are also introduced continuously into the beginning of the last fourth of the reactor. A freely flowing paste is obtained. For reaction conditions, see Table 3.

TABLE 3

| Example | 4A | 4B |
|---|---|---|
| Total throughput (kg/h) | 17 | 17 |
| Shaft speed (min$^{-1}$) | 300 | 175 |
| Housing temperatures (°C.) | 39 to 52 | 41 to 53 |
| Product outlet temperature (°C.) | 48 | 49 |
| Yield (%) | 68 | 82 |
| Solid particle size (μm) approx. | 2 × 10 | 3 × 15 |

What is claimed is:

1. A process for the continuous preparation of polyisocyanates containing uretdione groups comprising dimerizing aromatic polyisocyanates which are free from uretdione groups in the presence of catalysts which accelerate the dimerization of isocyanates, at −30° to 90° C. in a self-cleaning, coolable screw reactor with continuous feeding in of the free polyisocyanate and of the dimerization catalyst, and in the presence of from 3 to 90% by weight, based on the whole mixture, of an additive containing hydroxyl groups, which additive comprises either (i) a compound within the molecular weight range of from 62 to 10,000 containing at least one hydroxyl group or (ii) a mixture of several compounds having an average molecular weight within the range of from 62 to 10,000 containing at least one hydroxyl group, wherein said hydroxyl-containing compound or compounds are added to the reaction mixture before the completion of the dimerization reaction.

2. The process of claim 1, wherein said hydroxyl group-containing additive (i) is a polyhydroxyl compound containing 2 or 3 hydroxyl groups and having a molecular weight of from 400 to 6000 or (ii) is a mixture of compounds containing hydroxyl groups and having an average hydroxyl functionality of from 1.5 to 3 and an average molecular weight in the range of from 400 to 6000.

3. The process of claim 1, wherein the dimerization reaction is stopped by mixing the reaction mixture with a catalyst poison for the dimerization catalyst.

4. The process of claim 1, wherein the reaction mixture is mixed with additional polyisocyanates or compounds containing hydroxyl groups during or after completion of the dimerization reaction.

* * * * *